United States Patent
Altschul et al.

(10) Patent No.: US 8,263,328 B2
(45) Date of Patent: Sep. 11, 2012

(54) DEVICES AND FORMULATIONS FOR DETECTING, SCREENING AND MONITORING LEVELS OF CERTAIN CONSTITUENTS IN BODILY FLUIDS AND METHOD

(75) Inventors: Randice Lisa Altschul, Cliffside Park, NJ (US); Myron Rapkin, Indianapolis, IN (US); Rebecca O'Brien, Shell Knob, MO (US)

(73) Assignee: Pop Test LLC, Cliffside Park, NJ (US)

( * ) Notice: Subject to any disclaimer, the term of this patent is extended or adjusted under 35 U.S.C. 154(b) by 0 days.

(21) Appl. No.: 13/278,306

(22) Filed: Oct. 21, 2011

(65) Prior Publication Data
US 2012/0100563 A1    Apr. 26, 2012

Related U.S. Application Data

(60) Provisional application No. 61/455,528, filed on Oct. 23, 2010, provisional application No. 61/455,531, filed on Oct. 23, 2010, provisional application No. 61/455,532, filed on Oct. 23, 2010, provisional application No. 61/462,890, filed on Feb. 9, 2011.

(51) Int. Cl.
*C12Q 1/00* (2006.01)
(52) U.S. Cl. .................. 435/4; 435/14; 435/25
(58) Field of Classification Search ............. 435/4, 14, 435/25
See application file for complete search history.

(56) References Cited

U.S. PATENT DOCUMENTS

| | | | |
|---|---|---|---|
| 4,381,921 A * | 5/1983 | Pierce et al. | 436/535 |
| 4,935,346 A * | 6/1990 | Phillips et al. | 435/14 |
| 7,364,695 B2 * | 4/2008 | Rapkin et al. | 422/424 |
| 2003/0212344 A1 | 11/2003 | Yuzhakov et al. | |
| 2004/0158137 A1 | 8/2004 | Eppstein et al. | |
| 2007/0003993 A1 | 1/2007 | Kritzman et al. | |
| 2010/0166604 A1 | 7/2010 | Lim et al. | |

OTHER PUBLICATIONS

Ugwu et al. "The effect of buffers on protein conformational stability", Pharmaceutical Technology, 2004, pp. 86,88,90,92,94,96,98,100,102,104,106,108,110-113.*

* cited by examiner

*Primary Examiner* — Susan Hanley
*Assistant Examiner* — Bin Shen
(74) *Attorney, Agent, or Firm* — Arthur Jacob

(57) ABSTRACT

A device is disclosed for conducting a non-invasive analysis of a bodily fluid to determine the presence and level of a certain constituent carried by the bodily fluid. An indicator formulation of the device changes color in response to exposure to the constituent to provide a visible indication of the presence and level of the constituent carried by the bodily fluid. A carrier substrate of the device is constructed of a material having voids providing a high void volume within the substrate. The device is made by applying a chromagen to the carrier substrate to create a chromagen-laden carrier member. Then, a selected reagent having a particular constituent-specific formulation is applied to the chromagen-laden member. The selected reagent then combines with the chromagen, thereby establishing the indicator formulation within the carrier substrate in place for reception of a sample of the bodily fluid.

14 Claims, 3 Drawing Sheets

DEVICES AND FORMULATIONS FOR DETECTING, SCREENING AND MONITORING LEVELS OF CERTAIN CONSTITUENTS IN BODILY FLUIDS AND METHOD

CROSS-REFERENCE TO RELATED APPLICATIONS

This application claims the benefit of U.S. Provisional Patent Application Ser. No. 61/455,528, filed Oct. 23, 2010, U.S. Provisional Patent Application Ser. No. 61/455,531, filed Oct. 23, 2010, U.S. Provisional Patent Application Ser. No. 61/455,532, filed Oct. 23, 2010, and U.S. Provisional Patent Application Ser. No. 61/462,890, filed Feb. 9, 2011, the entire disclosures of which are incorporated herein by reference thereto.

BACKGROUND OF THE INVENTION

1. Field of the Invention

The present invention relates generally to devices and formulations for reagents employed in such devices that enable detecting, screening and monitoring levels of certain constituents in bodily fluids sampled from humans and animals, and pertains, more specifically, to the construction and manufacture of such devices.

2. Description of Related Art

In two earlier U.S. Pat. Nos. 7,824,344 and 7,993,283, the substance of which patents is incorporated herein by reference thereto, there is disclosed methods and apparatus for conducting a non-invasive analysis of saliva. The present invention provides formulations and devices that enable a user to employ a bodily fluid, such as saliva or another oral fluid, serum or plasma, utilizing devices that provide color changes to indicate the presence and level of a certain constituent in the bodily fluid. Further, the present invention provides methods of construction and manufacture that enable such devices to be made available for widespread use for detecting, screening or monitoring the presence and level of any one of a plurality of certain constituents with increased ease and economy. As such, the present invention attains several objects and advantages, some of which are summarized as follows: Provides devices of simplified construction for widespread use in detecting, screening and monitoring the presence and level of any selected one of a plurality of certain constituents in bodily fluids; enables an exceptionally rapid response in a quick and easy non-invasive procedure for determining the presence and level of a particular constituent in a bodily fluid; provides for the economical manufacture and distribution of devices capable of detecting, screening and monitoring the presence of certain constituents in bodily fluids; makes available a simplified visual reading of a color change to determine the presence and level of a certain constituent in a bodily fluid; provides an economical and reliable device for simplified use in detecting, screening or monitoring the presence of a selected certain constituent in a bodily fluid; encourages widespread use to the benefit of a larger number of users who can enjoy greater economy and convenience in reaching and maintaining higher goals in healthcare.

BRIEF SUMMARY OF THE INVENTION

The above objects and advantages are attained by the present invention, which may be described briefly as a method of making a device for conducting a non-invasive analysis of a bodily fluid to determine the presence and the level of a certain constituent carried by the bodily fluid, the device including an indicator formulation capable of changing color in response to exposure to the certain constituent to provide a visible indication of the presence and the level of the certain constituent carried by the bodily fluid, the method comprising: providing a carrier substrate of a material having voids establishing a high void volume within the carrier substrate; applying a chromagen formulation to the carrier substrate to create a chromagen-laden carrier member; and subsequently applying to the chromagen-laden carrier member a selected reagent having a particular constituent-specific formulation to combine the selected reagent with the chromagen formulation applied to the carrier substrate, thereby establishing the indicator formulation within the carrier substrate in place for reception of a sample of the bodily fluid later placed upon the carrier substrate.

In addition, the invention provides a device for conducting a non-invasive analysis of a bodily fluid to determine the presence and the level of a certain constituent carried by the bodily fluid, the device including an indicator formulation capable of changing color in response to exposure to the certain constituent to provide a visible indication of the presence and the level of the certain constituent carried by the bodily fluid, the device comprising: a carrier substrate of a material having voids establishing a high void volume within the carrier substrate; and an indicator formulation carried by the carrier substrate, the indicator formulation consisting essentially of a chromagen formulation and a constituent-specific formulation selected from formulations responsive to levels of any one of a plurality of different certain constituents.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing, in which.

DETAILED DESCRIPTION OF THE INVENTION

Figure 1:
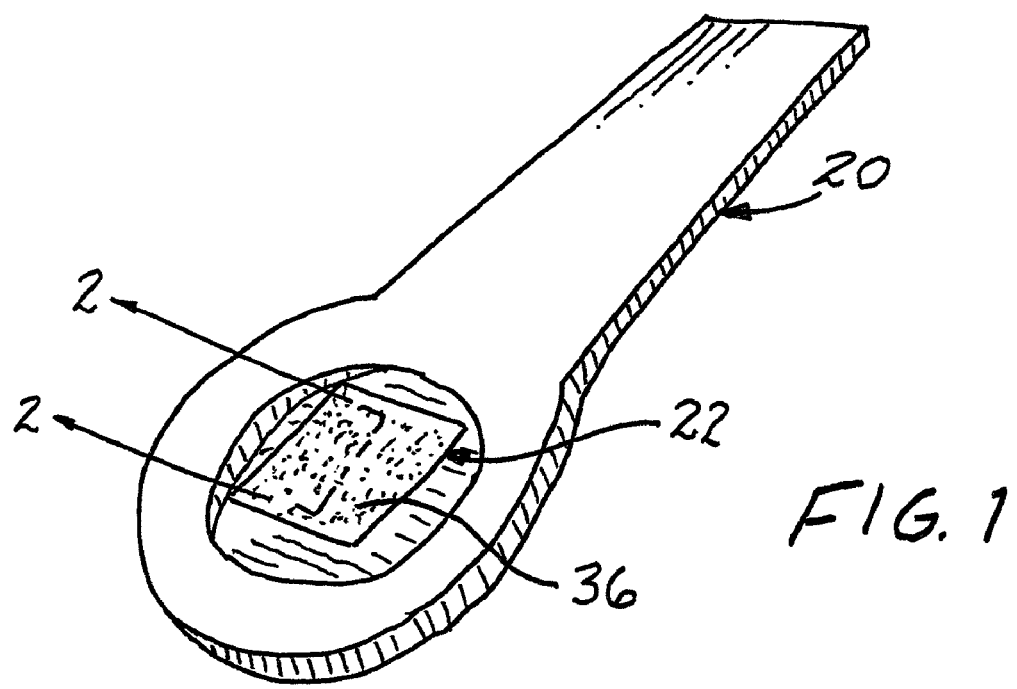
FIG. 1 is a pictorial view of a device constructed in accordance with the present invention.
Figure 2:
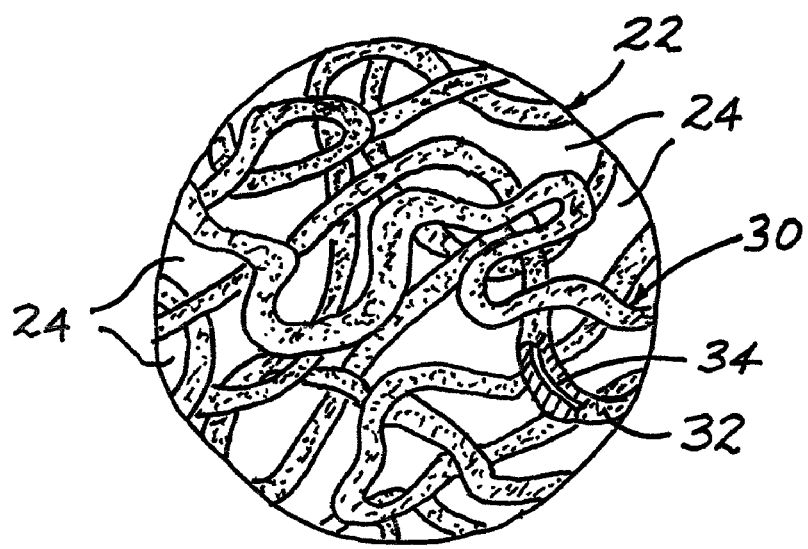
FIG. 2 is an enlarged, somewhat diagrammatic, cross-sectional view taken along line 2-2 of FIG. 1.

Referring now to the drawing, and especially to FIGS. 1 and 2 thereof, a device constructed in accordance with the present invention is shown at 20 and is seen to include a carrier substrate in the form of a pad 22 of a material having voids 24 establishing a high void volume within the pad 22. An indicator formulation is carried by the pad 22 and is illustrated at 30 in the form of a layer 32 carried by fibers 34 of the material, in juxtaposition with voids 24 within the pad 22. Indicator formulation 30 consists essentially of a chromagen formulation and a reagent having a constituent-specific formulation selected from formulations responsive to one of a plurality of constituents, as will be set forth in greater detail below. Suffice it to say at this juncture that the reagent having a constituent-specific formulation and the chromagen formulation are combined within the pad 22 such that the indicator formulation 30 is capable of changing color in response to exposure to the certain constituent to provide a visible indication on the pad 22 of the presence and the level of the certain constituent carried by a sample of a bodily fluid applied to the pad 22.

Thus, upon applying a sample of a bodily fluid, such as a saliva sample, to the pad 22, placed at a target area 36 of the device 20, the occurrence of a visible color change will provide at least a qualitative indication of the presence of the particular specific constituent to which the constituent-specific formulation will react. An absence of any visible color change will indicate that the specific constituent is not present in any significant amount in the saliva sample.

The preferred material for pad 22 is a non-woven fibrous material which provides the requisite high void volume. The high void volume provides pad 22 with the ability to absorb rapidly the sample of bodily fluid applied to the target area 36, to enable rapid interaction of the sample with the indicator formulation 30, and to maximize exposure of the interacting sample and indicator formulation to ambient air for promoting a quick response through accelerating a reaction between the certain constituent carried by the sample and the indicator formulation. Non-woven synthetic polymeric materials are available commercially, one such material being a non-woven polyester fibrous material. Suitable glass-fiber non-woven fibrous materials and cellulose non-woven fibrous materials also are available commercially in forms suitable for use in the construction of pad 22. The preferred materials are chosen to provide pad 22 with a void volume within a range of about eight to twelve percent of the total volume of the material.

Device 20 is constructed in several different variations such that one variation is available to provide a visible color change as an indication of at least the presence of a corresponding one of several certain constituents, namely, glucose, cholesterol, ethanol, uric acid and galactose, and, preferably, the level of the certain constituent, in the sample of bodily fluid applied to the target area 36 of the pad 22. Each variation requires that the pad 22 carry a formulation specific to the constituent to be detected, as a component of the indicator fromulation 30; however, the chromagen formulation remains unchanged among the different variations of the pad 22 so that the same chromagen formulation can serve in every variation of the pad 22. Accordingly, the manufacture and distribution of the devices 20 is simplified and rendered more economical, as will be described below.

Figure 3:
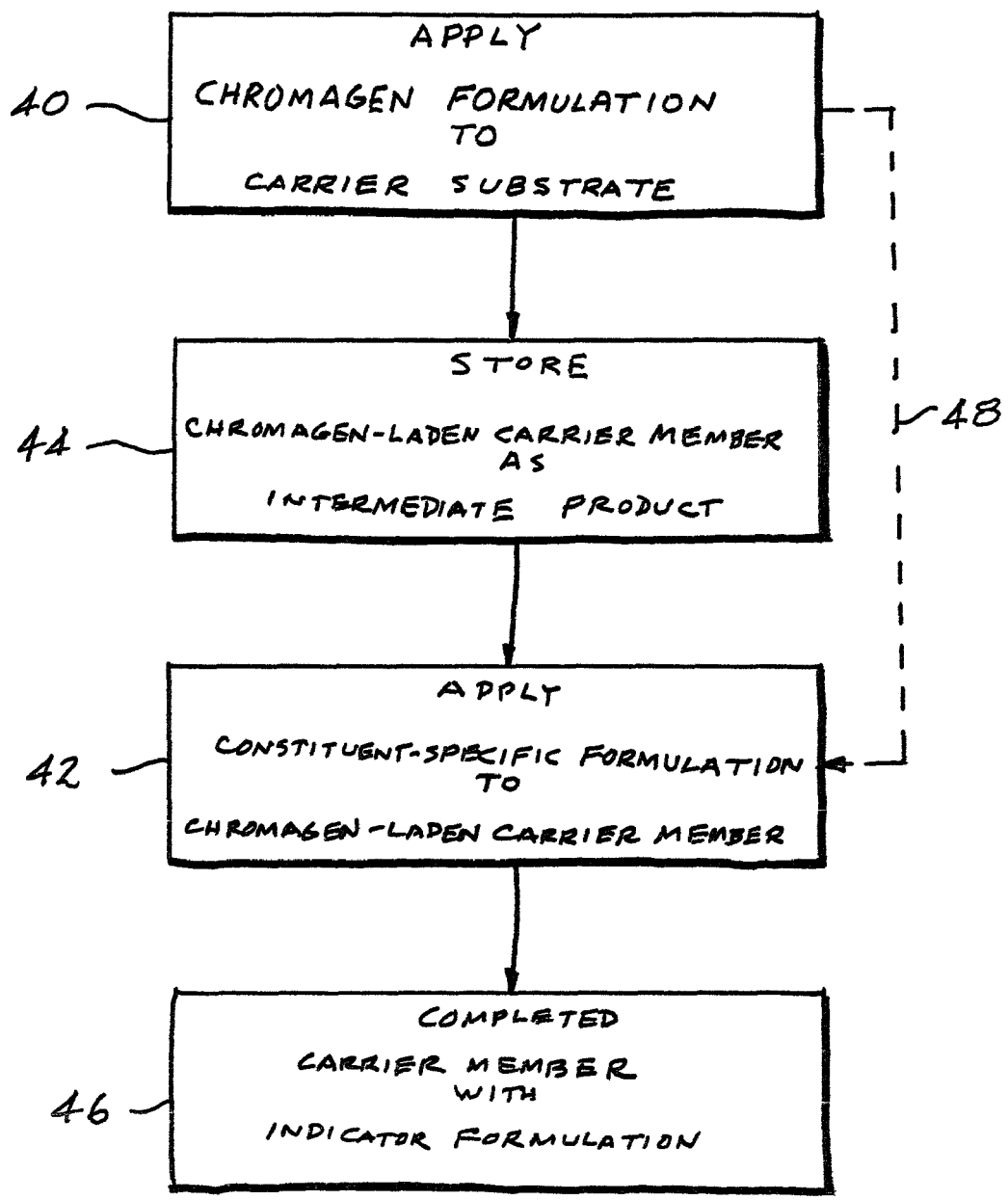
FIG. 3 is a flow diagram illustrating a method of the present invention.

Turning now to FIG. 3, as well as to FIGS. 1 and 2, pad 22 of device 20 is manufactured by first applying to the material of pad 22 the chromagen formulation, as seen in step 40, to create a chromagen-laden carrier member in the form of pad 22 with the chromagen formulation placed in juxtaposition with voids 24 of the pad 22. Subsequently, a selected reagent having a particular constituent-specific formulation is applied to the chromagen-laden carrier member, as indicated at step 42, to combine the selected reagent with the chromagen formulation applied earlier to the material of pad 22, thereby establishing the indicator formulation 30 within the completed pad 22. Pad 22 is placed at target area 36 of device 20 for reception of the sample of bodily fluid upon the pad 22. Since the chromagen formulation remains the same for all variations of the device 20, economies are realized in the manufacturing process which requires only one component common to all variations and only one station for the application of that common component; however, further economy and convenience are accomplished by the ability to store the intermediate product, that is, the material of pad 22 with the applied chromagen formulation, is stored, as seen in step 44. Subsequently applying any selected one of the constituent-specific formulations is applied, at a later time, in accordance with the requirement for any number of a particular device or particular devices, the completed carrier member with the indicator formulation being available at step 46. The ability to have on hand a supply of the basic chromagen-laden carrier member for subsequent combination with a selected constituent-specific formulation, as opposed to immediately creating an inventory of completed carrier members, as indicated by procedure 48, reduces the necessity for maintaining on-hand a large inventory of every variety of completed device 20 while increasing the flexibility and turn-around time of filling the demand for any number of devices 20 in any one of the different varieties.

With respect to the varieties identified above, the common chromagen formulation consists essentially of the following components, in an example prepared as follows: Approximately equal volumes of about 0.05 to 0.5 M MBTH in distilled water is mixed with about 0.05 to 0.5 M DMAB in ethanol. The mixture is impregnated into the material of the carrier member and the impregnated material subsequently is dried, leaving the material with the chromagen formulation coated upon the fibers of the material.

With respect to each of the varieties identified above, the following constituent-specific formulations are effective, and an example of the preparation of each is set forth below:

For the determination of the presence and level of glucose as the certain constituent in a bodily fluid, a constituent-specific formulation consists essentially of the following components, in an example prepared as follows: Dissolve approximately equal amounts of the enzymes glucose oxidase with an activity of approximately 200 U/mg and peroxidase with an activity of approximately 200 U/mg in distilled water in the presence of approximately equal amounts of 0.05 to 0.5 M HEPES, a blend of surface active agents within the range of about 0.1% to 10% each, and a stabilizer, the preferred stabilizer being a PVP/copolymer complex in which the copolymer is methylvinylether/maleic anhydride, available commercially under the trademark GANTREZ®, the complex being prepared from 5% PVP K30 in distilled water and 5% GANTREZ® AN 139 at a pH of about 7.5. The prepared constituent-specific formulation then is impregnated into the material previously impregnated with the chromagen formulation to complete a pad 22 having an indicator formulation 30 responsive to the presence and level of glucose in an applied sample of a bodily fluid.

For the determination of the presence and level of cholesterol as the certain constituent in a bodily fluid, a constituent-specific formulation consists essentially of the following components, in an example prepared as follows: Dissolve approximately equal amounts of the enzymes cholesterol esterase with an activity of approximately 180 U/mg and peroxidase with an activity of approximately 200 U/mg and twice as much cholesterol oxidase with an activity of approximately 47 U/mg) in distilled water in the presence of approximately equal amounts of 0.05 to 0.5 M HEPES, a blend of surface active agents within the range of about 0.1% to 10% each and a stabilizer, the preferred stabilizer being a PVP/copolymer complex in which the copolymer is methylvinylether/maleic anhydride, available commercially under the trademark GANTREZ®, the complex being prepared from 5% PVP K30 in distilled water and 5% GANTREZ® AN 139 at a pH of about 7.5. The prepared constituent-specific formulation then is impregnated into the material previously impregnated with the chromagen formulation to complete a pad 22 having an indicator formulation 30 responsive to the presence and level of cholesterol in an applied sample of a bodily fluid.

For the determination of the presence and level of ethanol as the certain constituent in a bodily fluid, a constituent-specific formulation consists essentially of the following components, in an example prepared as follows: Mix together approximately equal amounts of about 1% to 20% PVP K30 in distilled water, about 0.5% to 5% ethoxylated surfactant in distilled water and about 0.05 to 0.5 M phosphate buffer at pH 8.5 together with one-half the same amount of alcohol oxidase with an activity of approximately 400 U/ml and one-quarter the same amount of peroxidase with an activity of approximately 200 U/mg. The prepared constituent-specific formulation then is impregnated into the material previously impregnated with the chromagen formulation to complete a pad 22 having an indicator formulation 30 responsive to the presence and level of ethanol in an applied sample of a bodily fluid.

For the determination of the presence and level of uric acid as the certain constituent in a bodily fluid, a constituent-specific formulation consists essentially of the following components, in an example prepared as follows: In approximately one-hundred ml of 0.05 to 0.5 M phosphate buffered saline at pH 6.4, mix together approximately ten mg of uricase, fifteen mg of ascorbate oxidase and about six mg of peroxidase with an activity of approximately 200 U/mg. The prepared constituent-specific formulation then is impregnated into the material previously impregnated with the chromagen formulation to complete a pad 22 having an indicator formulation 30 responsive to the presence and level of uric acid in an applied sample of a bodily fluid.

For the determination of the presence and level of galactose as the certain constituent in a bodily fluid, a constituent-specific formulation consists essentially of the following components, in an example prepared as follows: Mix together approximately five ml each of about 0.05 to 0.5 M phosphate buffer at pH 7.0, peroxidase with an activity of about 200 U/mg, and ethanol (95%) together with about twenty-five ml of 10% polyvinyl alcohol in distilled water and 4200 units of galactose oxidase. The prepared constituent-specific formulation then is impregnated into the material previously impregnated with the chromagen formulation to complete a pad 22 having an indicator formulation 30 responsive to the presence and level of galactose in an applied sample of a bodily fluid.

Figure 4:
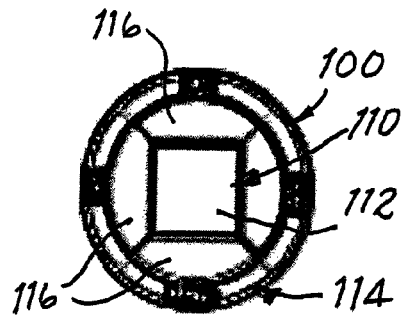
FIG. 4 is a plan view of another device constructed in accordance with the present invention.
Figure 5:
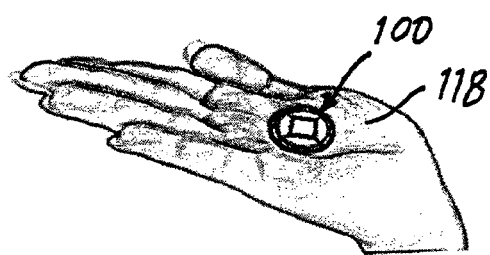
FIG. 5 is a pictorial view showing use of the device of FIG. 4.

In the embodiment of the invention illustrated in FIG. 4, a disk-shaped device 100 includes a pad 110 constructed of the material previously described in connection with pad 22 of device 20. Pad 110 provides a target area 112 which, in device 110, is substantially surrounded by an integrated color gauge 114 having patches 116 of different colors that can be matched visually with a color change at the target area 112. As in the devices disclosed in the aforesaid patents, U.S. Pat. Nos. 7,824,344 and 7,993,283, alpha-numeric characters may be displayed in juxtaposition with the patches 116 for a direct reading of the level detected. In this manner, device 100 provides a simple semi-qualitative/semi-quantitative measure of the presence and level of a particular certain constituent carried by a sample of bodily fluid applied to the target area 112. The semi-qualitative/semi-quantitative indication, while more comprehensive than the generally qualitative indication provided by device 20 described above, is convenient, as shown in FIG. 5 where the device 100 is placed readily within the palm 118 of a user's hand, but not as comprehensive as the indication provided by other embodiments of the invention, as set forth below.

Figure 6:
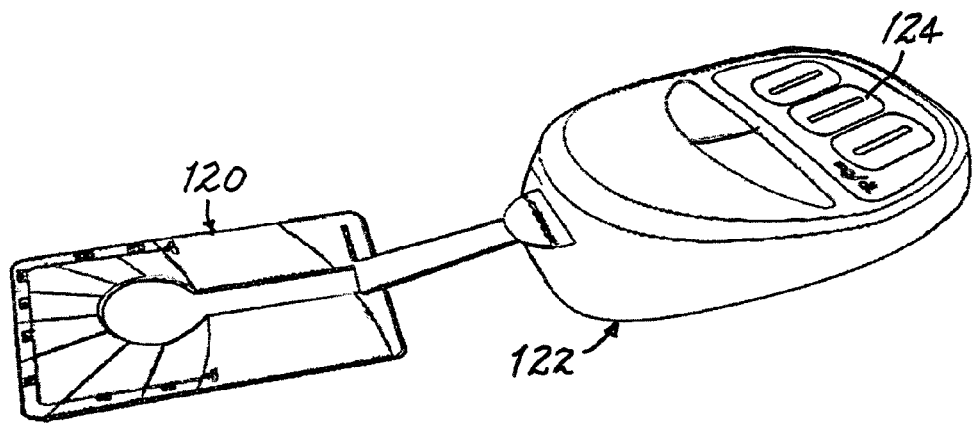
FIG. 6 is a pictorial view showing the use of still another device constructed in accordance with the present invention.

In the embodiment shown in FIG. 6, a device 120 is constructed as described in detail in the aforesaid patents, U.S. Pat. Nos. 7,824,344 and 7,993,283, and is inserted into a reader 122 that employs an algorithm which converts a sensed color change into an accurate digital readout at a display 124, for a more accurate quantitative evaluation of the presence and level of a particular certain constituent carried by a bodily fluid sample.

Figure 7:
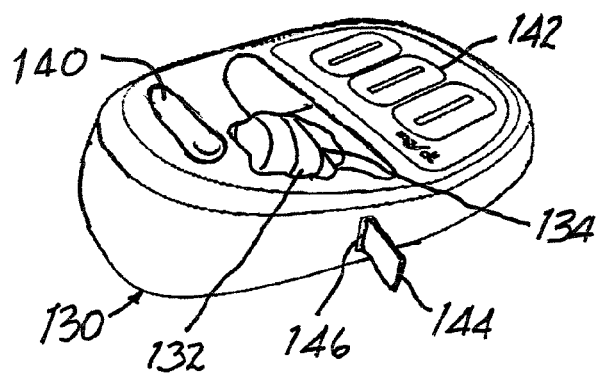
FIG. 7 is a pictorial view showing the use of yet another device constructed in accordance with the present invention.

In the embodiment illustrated in FIG. 7, a device 130 carries a strip 132 similar in construction to pad 22 described above, and arranged in a coil 134 held within the device 130. A sample of bodily fluid is applied to the strip 132, at a target area registered with an access door 140 through which the sample is passed to the strip 132. A color change is sensed and an algorithm converts the sensed color change into an accurate digital readout at a display 142. The used portion 144 of the strip 132 is advanced through a slot 146 and is torn off and discarded.

The embodiments illustrated in FIGS. 6 and 7 are conveniently available to a user wishing to control and maintain weight levels. Thus, for example, upon use of a device 120 or 130 in connection with monitoring the level of glucose in a bodily fluid, such as saliva, the algorithms provided by these embodiments can convert the detected glucose level into glycemic control readily understood and employed by a user in connection with a weight control regimen. In this manner, the user is provided with information to refine glycemic control, enabling the user to adjust diet, supplement intake and exercise for the purpose of glycemic control and weight control.

It will be seen that the present invention attains all of the objects and advantages summarized above, namely: Provides devices of simplified construction for widespread use in detecting, screening and monitoring the presence and level of any selected one of a plurality of certain constituents in bodily fluids; enables an exceptionally rapid response in a quick and easy non-invasive procedure for determining the presence and level of a particular constituent in a bodily fluid; provides for the economical manufacture and distribution of devices capable of detecting, screening and monitoring the presence of certain constituents in bodily fluids; makes available a simplified visual reading of a color change to determine the presence and level of a certain constituent in a bodily fluid; provides an economical and reliable device for simplified use in detecting, screening or monitoring the presence of a selected certain constituent in a bodily fluid; encourages widespread use to the benefit of a larger number of users who can enjoy greater economy and convenience in reaching and maintaining higher goals in healthcare.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A method of making a device for conducting a non-invasive analysis of a bodily fluid to determine the presence and the level of a certain constituent carried by the bodily fluid, the device including an indicator formulation capable of changing color in response to exposure to the certain constituent in the presence of ambient air to provide a visible indication of the presence and the level of the certain constituent carried by the bodily fluid, the method comprising:

providing a target area on a carrier substrate of a fibrous material having fibers and voids in a high void volume in juxtaposition with the target area and with fibers within the carrier substrate, with voids establishing communication between fibers and ambient air;

wherein the carrier substrate has a total volume and the high void volume is within a range of about eight to twelve percent of the total volume;

applying a chromagen formulation to fibers of the carrier substrate to create a chromagen-laden carrier member wherein applied chromagen formulation carried on fibers is placed in juxtaposition with voids in the carrier substrate for enabling exposure to ambient air within the voids; and subsequently applying to the chromagen formulation carried on fibers of the chromagen-laden carrier member a selected reagent having a particular constituent-specific formulation to combine the selected reagent with the chromagen formulation on fibers of the carrier member, thereby establishing the indicator formulation on fibers of the carrier member, in juxtaposition with voids within the carrier substrate and with the target area, in place for communication with ambient air within the voids and reception of a sample of the bodily fluid later placed upon the target area of the carrier substrate and in communication with ambient air within the voids for enabling reaction with the indicator formulation on the fibers, with the sample exposed to ambient air present in the juxtaposed voids as the certain constituent in the sample reacts with the indicator formulation.

2. The method of claim 1 including storing the chromagen-laden carrier member for a subsequent application of the selected reagent at a selected future time, removing from storage the chromagen-laden carrier member at the selected future time, selecting a reagent from reagents having formulations responsive to levels of any one of a plurality of different certain constituents, and then applying the so selected reagent to the removed chromagen-laden carrier member.

3. The method of claim 1 wherein the fibrous material of the carrier substrate comprises a non-woven material.

4. The method of claim 1 wherein the fibrous material of the carrier substrate comprises a non-woven synthetic polymeric material.

5. The method of claim 4 wherein the synthetic polymeric material is a polyester.

6. The method of claim 1 wherein the material of the carrier substrate comprises glass-fiber.

7. The method of claim 1 wherein the chromagen formulation remains the same, while the selected reagent having a constituent-specific formulation is selected from reagents having formulations responsive to levels of any one of a plurality of different certain constituents.

8. The method of claim 7 wherein the certain constituent is any one of glucose, cholesterol, ethanol, uric acid, or galactose.

9. The method of claim 1 wherein the chromagen formulation consists essentially of approximately equal parts of 0.05 to 0.5 M 3-methyl-2-benzothiazolinone hydrazone and 0.05 to 0.5 M dimethylaminobenzoic acid.

10. The method of claim 9 wherein the certain constituent is glucose and the constituent-specific formulation consists essentially of approximately equal amounts of glucose oxidase with an activity of approximately 200 U/mg, and peroxidase with an activity of approximately 200 U/mg in the presence of approximately equal amounts of 0.05 to 0.5 M HEPES, a blend of surface active agents within the range of about 0.1% to 10% each, and a stabilizer.

11. The method of claim 9 wherein the certain constituent is cholesterol and the particular constituent-specific formulation consists essentially of a selected amount of cholesterol esterase with an activity of approximately 180 U/mg, the same selected amount of peroxidase with an activity of approximately 200 U/mg, and twice the selected amount of cholesterol oxidase with an activity of approximately 47 U/mg in the presence of approximately equal amounts of 0.05 to 0.5 M HEPES, a blend of surface active agents within the range of about 0.1% to 10% each, and a stabilizer.

12. The method of claim 9 wherein the certain constituent is ethanol and the particular constituent-specific formulation consists essentially of approximately equal selected amounts of about 1% to 20% PVP K30, about 0.5% to 5.0% ethoxylated surfactant and about 0.05 to 0.5 M phosphate buffer at pH 8.5, one-half the selected amount of alcohol oxidase with an activity of approximately 400 U/ml and one-quarter the selected amount of peroxidase with an activity of approximately 200 U/mg.

13. The method of claim 9 wherein the certain constituent is uric acid and the particular constituent-specific formulation consists essentially of approximately ten parts of uricase, about fifteen parts of ascorbate oxidase and about six parts of peroxidase with an activity of approximately 200 U/mg in 0.05 to 0.5 M phosphate buffered saline at pH 6.4.

14. The method of claim 9 wherein the certain constituent is galactose and the particular constituents-specific formulation consists essentially of approximately five parts of about 0.05 to 0.5 M phosphate buffer at pH 7.0, approximately five parts of peroxidase with an activity of approximately 200 U/mg, and approximately five parts of ethanol, in about twenty-five parts of 10% polyvinyl alcohol, and 4200 units of galactose oxidase.

* * * * *